(12) United States Patent
Tu et al.

(10) Patent No.: US 8,475,845 B2
(45) Date of Patent: Jul. 2, 2013

(54) METHOD OF PARTICLE FORMATION

(75) Inventors: Linda Sze Tu, North Ryde (AU);
Hubert Leonardus Regtop, Mittagong (AU); Neil Russell Foster, St. Ives (AU);
Pascal Hickey, North Ryde (AU)

(73) Assignee: MAP Pharmaceuticals, Inc., Mountain View, CA (US)

(*) Notice: Subject to any disclaimer, the term of this patent is extended or adjusted under 35 U.S.C. 154(b) by 862 days.

(21) Appl. No.: 11/995,676

(22) PCT Filed: Jul. 14, 2006

(86) PCT No.: PCT/US2006/000998
§ 371 (c)(1),
(2), (4) Date: Jan. 14, 2008

(87) PCT Pub. No.: WO2007/009164
PCT Pub. Date: Jan. 25, 2007

(65) Prior Publication Data
US 2009/0004282 A1    Jan. 1, 2009

Related U.S. Application Data

(60) Provisional application No. 60/669,734, filed on Jul. 15, 2005.

(51) Int. Cl.
| B01J 2/06 | (2006.01) |
| A61K 31/567 | (2006.01) |
| A61K 31/167 | (2006.01) |
| A61K 31/58 | (2006.01) |
| A61K 31/137 | (2006.01) |

(52) U.S. Cl.
USPC ............... 424/490; 210/511; 514/171

(58) Field of Classification Search
None
See application file for complete search history.

(56) References Cited

U.S. PATENT DOCUMENTS

| 5,043,280 A | 8/1991 | Fischer et al. ............... 435/235 |
| 5,301,664 A | 4/1994 | Sievers et al. ............ 128/200.23 |
| 5,639,441 A | 6/1997 | Sievers et al. .................. 424/9.3 |
| 5,833,891 A | 11/1998 | Subramaniam et al. ........... 264/7 |
| 5,851,453 A | 12/1998 | Hanna et al. ..................... 264/5 |
| 5,874,029 A | 2/1999 | Subramaniam et al. ........ 264/12 |
| 6,030,604 A * | 2/2000 | Trofast .......................... 424/46 |
| 6,063,138 A | 5/2000 | Hanna et al. .................... 23/295 |
| 6,087,003 A | 7/2000 | Benoit et al. .................. 428/403 |
| 6,183,783 B1 | 2/2001 | Benoit et al. ................... 424/497 |
| 6,221,398 B1 | 4/2001 | Jakupovic et al. ............. 424/489 |
| 7,780,991 B2 * | 8/2010 | Roser et al. .................... 424/499 |
| 2001/0007669 A1 | 7/2001 | Liu et al. ......................... 424/400 |
| 2004/0043076 A1 | 3/2004 | Dulieu et al. .................. 424/490 |
| 2006/0182808 A1 * | 8/2006 | Bakker et al. ................. 424/489 |
| 2006/0258798 A1 * | 11/2006 | Richard et al. ................ 524/544 |

FOREIGN PATENT DOCUMENTS

| AU | 784168 | 8/2000 |
| EP | 1 016 454 | 12/1999 |
| WO | WO 95/01324 | 1/1995 |
| WO | WO 96/00610 | 1/1995 |
| WO | 96/00610 | * 1/1996 |
| WO | WO 98/17676 | 4/1998 |
| WO | WO 98/36825 | 8/1998 |
| WO | WO 98/52544 | 11/1998 |
| WO | WO 98/58722 | 12/1998 |
| WO | WO 99/44733 | 9/1999 |
| WO | WO 99/59710 | 11/1999 |
| WO | WO 00/30612 | 2/2000 |
| WO | WO 00/30613 | 2/2000 |
| WO | WO 00/30614 | 2/2000 |
| WO | WO 00/37169 | 6/2000 |
| WO | 01/03821 | * 1/2001 |
| WO | WO 01/03821 | * 1/2001 |
| WO | WO 01/12160 | 2/2001 |
| WO | WO 01/60341 | 8/2001 |
| WO | WO 01/66091 | 9/2001 |
| WO | WO 02/38127 | 5/2002 |
| WO | WO 02/058674 | 8/2002 |
| WO | WO 02/092213 | 11/2002 |
| WO | WO 03/004142 | 1/2003 |
| WO | WO 03/008082 | 1/2003 |
| WO | WO 2004/091571 | 10/2004 |

OTHER PUBLICATIONS

York, "Strategies for particle design using supercritical fluid technologies", PSTT, 2(11):430, 1999.

* cited by examiner

*Primary Examiner* — Suzanne Ziska
(74) *Attorney, Agent, or Firm* — DLA Piper LLP (US)

(57) ABSTRACT

A method of co-formulating two or more pharmaceutically active compounds into a particulate product including contacting a dense, supercritical or near-critical fluid With a suspension of a first active compound in a medium that is miscible with the dense fluid and a solution of a second active compound in a solvent that is miscible with the dense fluid. The product may be the first active agent coated with the second active agent. The method may use coaxial nozzles for the fluid, media or solvents. The method may be applied to production of dry powders for inhalation including beta-agonists and corticosteroids. Apparatus for use in the method comprising means for streams of solvents, media and dense fluids to enter a precipitation chamber at substantially the same point and means for collection of particles under gravity in one or more collection chambers.

26 Claims, 10 Drawing Sheets

METHOD OF PARTICLE FORMATION

CROSS REFERENCE TO RELATED APPLICATIONS

This application is a 35 USC §371 National Stage application of PCT Application No. PCT/AU2006/000998 filed Jul. 14, 2006; which claims the benefit under 35 USC §119(e) to U.S. Application Ser. No. 60/699,734 filed Jul. 15, 2005, now abandoned. The disclosure of each of the prior applications is considered part of and is incorporated by reference in the disclosure of this application.

FIELD OF THE INVENTION

The present invention relates generally to the production of a particulate product including two or more pharmaceutically active compounds in a stable micron-sized form with substantially uniform morphology and mass ratio. It may be used for the formation of particles containing an antiinflammatory agent and a bronchodilator agent. Such particles may, for example, be suitable for administration by inhalation.

BACKGROUND OF THE INVENTION

Reference to any prior art in the specification is not, and should not be taken as, an acknowledgement of any form of suggestion that this prior art forms part of the common general knowledge in Australia or any other jurisdiction or that his prior art would reasonably be expected to be ascertained, understood and regarded as relevant by a person skilled in the art.

Conventional techniques for production of fine particulate preparations (also called particulate products) suffer from many disadvantages. These conventional methods involve either mechanical comminution (crushing, grinding, and milling), or precipitation or recrystallisation of the solute from liquid solutions. The production of particles of less than 5 µm is most usually achieved by comminution of larger crystal material.

Micronisation by high energy processes such as grinding and milling can result in mechanically induced damage to the crystal structure manifesting as amorphous regions on the surface of the particles. As a result the particles are usually highly charged, hygroscopic and/or cohesive.

Conventional recrystallisation (eg U.S. Pat. No. 6,221,398) of solutes from liquid solutions exploits the dependence of a compound's solubility on temperature and/or mixture composition. Crystallisation by either solvent evaporation or solvent extraction of a solute usually requires the use of toxic organic antisolvents and surfactants, and yields wet particles that require further drying to remove traces of adsorbed solvent residues. Furthermore there is limited scope to control the precipitation process, and thus the particles produced are commonly larger than required, and of a broad particle size range distribution.

Freeze drying is another technique for the production of solid preparations and products. A solution or suspension of pharmaceutical ingredients is snap-frozen, and then the solvent is removed by sublimation under conditions of low pressure and/or temperature. However, this process usually results in a product that is described as an amorphous cake, which does not normally comprise discrete particles which would be required, for example, for effective inhalational delivery.

Another alternative method is spray drying, where a solution or suspension of pharmaceutical ingredients is sprayed into a chamber, the particles being produced though evaporation of the solvent in a hot air-fluidized bed. The high temperatures can degrade sensitive drugs and polymers, and the technique does not lend itself to the close control of product morphology during process scale-up. The method may also produce amorphous particles, which may have stability problems and a high tendency towards moisture reabsorption.

Supercritical Fluid (SCF) Technologies have advanced over the last decade, driven by the need for high purity drugs with controlled morphology. The most frequently used SCF process is the Aerosol Solvent Extraction System (ASES) process. The typical ASES process involves a continuous flow of solution containing a substance to be precipitated and the supercritical fluid being co-introduced into a particle formation vessel. This leads to simultaneous dispersion and mixing of the solution, rapid supersaturation and particle nucleation and formation of particles. Process conditions such as temperature, pressure, flow rates and type of solvent and antisolvent determine the morphology of the resulting particles. An example of an antisolvent commonly used in this process is carbon dioxide and the solvent may be chosen from a wide range of solvents in which the drug is soluble, and where the solvent is miscible with the antisolvent.

The simplest approach for the preparation of a particulate product containing two or more pharmaceutical ingredients is to mix the individual components by physical blending. Physical blending is commonly used to prepare particulate preparations for inhalation by dry powder inhalers. The difficulty in achieving consistent, homogenous mixtures using this approach is well recognised by the pharmaceutical industry and regulatory bodies.

Furthermore, the individual components of a physical mixture may separate over time; especially with processing, handling and administration, because of differences in particle morphology of the different ingredients. Such separation of components within a bulk mixture may lead to dosage inconsistencies and is therefore problematic.

An example of an existing method for the production of a combination particulate product is contained in US patent application no 20040028619. Therein a method is described where two drugs were dissolved in a mutual solvent in the desired ratio and the resultant liquid feed stock was atomised using an ultrasonic atomiser. The resultant droplets were suspended in a nitrogen carrier gas which was passed through a heated flow reactor. The particles that formed were collected using an electrostatic precipitator. However, there was evidence that the particles were of inconsistent morphology which is not desirable for many drug delivery applications.

Accordingly, it would be an advance in the art if a process could be developed for the production of particles of a combination product (ie, a product containing two or more pharmaceutically active compounds); the particles preferably having a small particle size, a narrow particle size distribution, and the active compounds in a crystalline form. It would be a further advance in the art if the combination product could be produced in essentially one step, and, for example, have superior aerodynamic properties over a combination product for inhalation produced by physical mixing.

SUMMARY OF THE INVENTION

According to one aspect of the present invention, there is provided a method of coformulating two or more pharmaceutically active compounds into a particulate product, the method including contacting a dense fluid with:

a suspension of a first active compound in a suspension medium that is miscible with the dense fluid; and a solution of a second active compound in a solvent that is miscible with the dense fluid;

such that precipitation of the second active in the presence of the first active is induced. The particles of the particulate product may, for example, have a predetermined morphology such that they may be effectively administered by inhalation. The "morphology" of the particles in this context has different aspects, including the size and shape of particles, and also the crystal form of the active(s) in the particulate product. In respect of each of these, uniformity (within a reasonable tolerance) of particle size or shape may be achieved, as well as the desired size range.

In a preferred embodiment of the present invention, the dense fluid is an antisolvent. The precipitation of the product is induced by combining the dense fluid, the solution and the suspension. Without being bound by any theory or mode of action, it is believed that the precipitation occurs by the dense fluid acting as an antisolvent and simultaneously dispersing and extracting the suspension medium and the solvent from the first and second active compounds respectively.

The suspension medium and solvent may be of any suitable type provided that they are independently miscible with the dense fluid. The suspension medium and solvent may also be a combination of two or more solvents, provided that the combination of solvents is miscible with the dense fluid. In a preferred embodiment, the solvent for the second active compound is the same as the suspension medium for the first active compound.

In a preferred embodiment, the method produces particles of the first and second actives combined. Such particles have substantially uniform morphology and mass ratio. Preferably, at least most of the particles are of substantially uniform shape and/or substantially uniform size.

In one embodiment, the suspension of the first active compound and the solution of the second active compound are maintained separately prior to being contacted with the dense fluid.

In a preferred embodiment, the first and second active compounds may be any combination of pharmacologically active compounds. Exemplary active compounds for use in the present invention include, but not limited to, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antianxiety agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, bronchodilators (including β-agonists), cardiac inotropic agents, contrast media, corticosteroids (including mineral corticoids and glucocorticoids), cough suppressants (expectorants and mucolytics), diagnostic agents, diagnostic imaging agents, diuretics, dopaminergics (antiparkinsonian agents), haemostatics, immunological agents, metabolic replacement or supplements, lipid regulating agents, muscle relaxants, parasympathomimetics, parathyroid calcitonin and biphosphonates, prostaglandins, radiopharmaceuticals, sex hormones (including steroids), anti-allergic agents, sedatives, stimulants and anorectics, sympathomimetics, thyroid agents, vasodilators and xanthines. The first and second active compounds may be independently selected from the above.

In one embodiment, the first active is a bronchodilator. In a preferred embodiment, the first active is formoterol fumarate or salmeterol xinafoate. In another embodiment, the second active compound is a corticosteroid. In a preferred embodiment, the second active compound is budesonide or fluticasone propionate. In another embodiment, the first active is a bronchodilator agent (such as a β-agonist) and the second active is an antiinflammatory agent (such as a corticosteroid). In a preferred embodiment, the bronchodilator is formoterol fumarate or salmeterol xinafoate and the antiinflammatory agent is budesonide or fluticasone propionate. In one embodiment, the actives are formoterol and budesonide in the ratio of between 1:10 and 1:30, preferably 1:15 and 1:20, more preferably about 1:18, respectively.

In a preferred embodiment, the first and second active compounds may be different members within the above classes. In a further preferred embodiment, the first and second active compounds may be the same active compound, with the first and second active compounds comprising different salts, polymorphs, isomers, or other modifications. In an additional embodiment, the first and second active compounds may be the same active compound or members of the same class with different dissolution and release characteristics.

In one preferred embodiment, a surfactant is added either to the suspension of the first active compound or to the solution containing the second active compound. It was observed that the presence of surfactant formed particles of a more consistent size and shape, and/or increased yield. Suitable surfactants include:

- non-ionic surfactants (short chain ethoxylated alcohols, polyethylene glycols, polyethoxy esters, polyvinyl alcohols glycerol esters and sorbitan esters)—suitable examples are Tween 80, Triton X-100, Tween 20, PEG, Span 60;
- anionic surfactants (phospholipids, sphingomyelins, ceramides and alkyl sulfates)—suitable examples are lecithin, sodium dodecyl sulfate, sodium lauryl sulfate;
- cationic (ureas and carbamides) like allantoin, hydantoin, diacylethoxy urea; and zwitterionic, such as aminopropryonic acid, dodecyl betaine, CHAPS.

The term "dense fluid" as used herein is used to refer generally to a fluid substantially near or above its critical pressure (Pc) and temperature (Tc). The pressure of the fluid will usually be in the range (0.9-3.0)Pc and its temperature (0.9-3.0)Tc, but these are examples of typical ranges, not limiting examples. In one embodiment, the dense fluid is used at (0.9 to 1.5)Pc and (1.0 to 1.5)Tc.

In this specification, there is reference to a "suspension" of a first active and a "solution" of a second active. It will be appreciated by one skilled in the art that the meaning of these terms is, to some extent, relative. An active that is soluble will form a "solution" and one that is insoluble will usually form a "suspension" but there may be a question of degree where, for example, an active is only soluble to a very small degree. In such a situation, it may be that part of the active is in solution and the rest remains as a suspension. Similarly, a highly dispersed active, particularly one with small particles, that technically could be regarded as a suspension may practically behave like a solution. For the purposes of the description of this invention, the reference to a "solution of an active" requires that there is sufficient of the active that has been dissolved to be coformulated with the other actives. Similarly, an active is in a "suspension" for the purposes of the invention if it remains in a solid, usually crystalline, form even if there is a small amount which is technically dissolved. For practical purposes, the term "solution" in respect of an active compound generally means that at least about 0.1% w/w of the solute is dissolved in the solvent under normal conditions. A non-solvent, such as a suspension medium for an active compound, is generally a fluid in which less than about 0.1% w/w of a compound is dissolved under the same conditions.

The dense fluid may be of any type, for example, $C_{1-4}$ alkanes (eg, ethane and propane), $C_{2-4}$ alkenes, $C_{2-4}$ alkynes, hydrofluoroalkanes, refrigerants (eg: RF134a), organic solvents (eg, ethanol and hexane), carbon dioxide, compressed air, nitrogen and the like, or two or more thereof. Carbon dioxide is preferred. The dense fluid may be an antisolvent for the second active compound.

Preferably, the method of the present invention produces a particulate product where there is physical interaction between the first active compound and the second active compound so as to promote enhanced delivery of the active compounds to the target organ or tissue. Preferably, the method of the present invention produces a particulate product where the physical interaction promotes the coincidental delivery of both active compounds to cells in the lung.

It is known that different drugs of different particle sizes will penetrate the lungs to different depths, in the case of drugs delivered by inhalation delivery. The term "coincidental delivery" as used herein refers to the delivery of the first active compound and the second active compound to the same cell in the target tissue, which is for inhalation delivery to the lung.

The mode(s) of interaction between the particles of the first active compound and the second active compound are not fully understood. Without wishing to be bound by any particular theory or mode of action, the physical interaction between the compounds may, for example, be due to the first active compound acting as a seed for the crystallisation of the second active compound. This may result in the formation of a particle containing the first active compound and the second active compound being bound together such that the crystals of the two compounds are interlinked and not easily separable. Even if one active does not seed crystallisation of another, the generally simultaneous formation of crystals of each in the method may result in particles of one active being physically or chemically engaged with another particle to form a combination or composite particulate material.

At one extreme of such a product, the first active compound may seed the precipitation of the second active compound in such a way that the first active compound is completely encased in the second active compound. Such a precipitation may naturally result in one active compound being coated in another active compound to differing degrees, from 1% to 100%. The surface of the coating may be a continuous coating over all or part of the surface of the former active compound. Alternatively, the coating may be discontinuous, leaving areas of the first active compound exposed. Where there is a significant coating, one active may be said to be partially or wholly "embedded" in the other.

Another possible way for there to be physical interaction between the first active compound and the second active compound is, for example, a situation where each particle contains only one active compound, either the first active compound or the second active compound. These particles may exist individually, or the individual particles may become bound to other particles in some manner. Such a situation may result in the formation of a particulate product material, each discrete particulate material containing two or more particles of the first active compound; or two or more particles of the second active compound; or one or more particles of the first active compound and one or more particles of the second active compound.

It will be appreciated that the above examples of physical interactions within the product of the method of the present invention are not exhaustive and should not be taken as limiting the scope of the meaning of the term "physical interaction".

The "bulk" or raw product resulting from the method of the present invention may contain exclusively one type of particle interaction, or a mixture of different forms of these particle interactions.

The terms "coformulating" and "coformulation" as used herein refer to the close physical interaction of the active compounds in the product, for example, as discussed above.

In a preferred embodiment of the present invention the first active compound is partially or fully coated by the second active compound in the resulting particles. For example, between at least 40% of the first active compound is coated in the second active compound. In other embodiments, the percentage of first active coated is about 45%, 50%, 60%, 65%, 70%, 75%, 80%, 85%, 90%, 95% or 100%.

In one embodiment, the method of the present invention allows for the adjustment of the concentration and/or flowrate of the suspension of the first active compound and/or the solution of the second active compound to produce a particulate product with the desired ratio of first active compound to second active compound in the bulk product, the ratio being between 1:1 and 1:100 (w/w). In one embodiment the mass ratio is between about 1:12 and 1:36 (w/w), preferably 1:15 to 1:25. In one form, the mass ratio of formoterol to budesonide is about 1:18.

In one embodiment the method produces a particulate product with physical properties such that the ratio of first active compound to second active compound is substantially maintained when it is dispersed and distributed across a system that separates the product largely on the basis of particle size. Examples of such a system include a device such as a cascade impactor test system and a human lung. The particulate product will usually contain particles of a range of sizes. The range of different particle sizes present in a particulate product may be measured using a device such as a cascade impactor, where the particulate product is dispersed and the product is separated largely according to the different particle sizes present in the product. A device such as a cascade impactor traps particles at different "stages" and in general, the smaller the particles, the further they progress through the device to be trapped at later "stages".

The particulate product may be suitable for any of nasal, pulmonary, transdermal or parenteral delivery. In one embodiment, it is suitable for pulmonary delivery.

In relation to particulate products to be used in inhalational delivery, particles of less than 5 micron in diameter are generally is desirable, as these particles should penetrate deeper into the lungs. For example, suitable particles would be trapped on Stages 3 to 8 on a cascade impactor device. Stages 3 to 8 of a cascade impactor device trap particles sized between 0.26 and 6.5 micron. This fraction of particles is known as the "fine particle fraction" (and sometimes as "effective particle size range"). In a preferred form, the bulk of the material by mass would be trapped on Stages 3 to 6 of the cascade impactor device. Stage 6 traps particles to a minimum size of 1.2 µm.

In an ideal product, the particulate product produced by the method of the present invention has an identical mass ratio of first active compound to second active compound across all particle size ranges, or Stages. In other words, each separate stage of the cascade impactor device would collect particular sized particles, the average actives mass ratio of which would be identical for each separate stage of the cascade impactor device. In practice, however, the average mass ratio of the particles collected on each stage of the cascade impactor device may not be identical and there may be some variance in the average mass ratio between the different stages. Accordingly, the present invention provides that at least 80%, preferably at least 90%, most preferably at least 95% of the fine particle fraction (see above) achieves the target mass ratio. In a most preferred embodiment, the entire particulate product achieves the target mass ratio. In other words, while maintaining a substantially identical mass ratio of active compounds across all particle size stages is preferred, achieving a narrow range (ie, within acceptable limits) of mass ratio of active compounds in each particle size stage (eg, between 1:10 and 1:30 in each stage of the fine particle fraction) will be an improvement over known particulate combinations. The acceptable level of variability (ie, the "within acceptable limits" referred to above) between the ratio of active compounds in different stages may be determined by experiment, or predicted based on the particular knowledge of the particular active compounds, based on the required pharmacological activity of the combination of active compounds. In other words, while maintaining an identical mass ratio of active compounds across all particle size stages is preferred, achieving a narrow range of mass ratio of active compounds in each particle size range will be an improvement over known particulate combinations.

In another embodiment, the first and second actives are formoterol and budesonide and at least 90%, preferably 95%, more preferably 100%, by mass, of the fine particle fraction (as classified by an Anderson cascade impactor device) has the desired ratio (eg, about 1:18 by mass). It is desirable that this ratio is substantially maintained when the particulate product is dispersed by, for example, a dry powder inhaler. Accordingly, the intention is that the bulk of the particles which actually deliver actives to a target site (eg, the lung cells) have the actives in the desired ratio. It will usually be convenient to define the ratio by mass, but it may equally be defined by molar amounts or other properties (eg where an active has a variable molecular weight).

The particles are preferably less than 10 µm in diameter, preferably less than 8 µm, more preferably less than 5 µm. In one embodiment, at least 90%, preferably at least 95%, are less than 7 µm in diameter. In these embodiments, at least 90%, preferably at least 95% of those particles also have a diameter greater than 0.5 µm. More preferably, at least 90%, preferably at least 95% of those particles have a diameter greater than 1 µm. Most preferably, at least 90%, preferably at least 95% of those particles have a diameter greater than 1.2 µm.

The method may be conducted at a temperature of between 0° C. and 100° C. More preferably, the temperature is between 10° C. and 80° C., most preferably 20° C. and 60° C. The method may be conducted at a pressure of between 1 bar and 500 bar. When the dense fluid is carbon dioxide, the method is preferably conducted at a pressure between 4 bar and 200 bar, most preferably between 50 bar and 150 bar. When the dense fluid is a refrigerant, the method is preferably conducted at a pressure in the lower end of the 1 bar to 500 bar pressure range.

The method may be conducted with a flowrate ratio of the suspension of the first active compound to the dense fluid of between about 1:10 to about 1:5000 (at operating temperature and pressure). Preferably the flowrate ratio is between about 1:50 and about 1:1000, most preferably between about 1:80 and about 1:200.

The method may be conducted with a flowrate ratio of the solution of the second active compound to the dense fluid of between about 1:10 to about 1:5000 (at operating temperature and pressure). Preferably the flowrate ratio is between about 1:50 and about 1:1000, most preferably between about 1:80 and about 1:200.

In one embodiment of the invention, the apparatus is adapted to generate laminar flow characteristics in the precipitation chamber. This facilitates particle formation in the chamber as particles of a predominantly toroidal morphology. Without being bound by any theory or mode of action, it is believed that deviations from a laminar flow regime in the precipitation chamber, such as transitional or turbulent flow, can lead to deviations from toroidal morphology in the product produced.

In another embodiment, there is provided a method of coformulating two or more pharmaceutically active compounds into a particulate product, the method consisting essentially of contacting a dense fluid with a suspension of a first active compound in a suspension medium that is miscible with the dense fluid; and a solution of a second active compound in a solvent that is miscible with the dense fluid; such that precipitation of the second active in the presence of the first active is induced. This embodiment also has preferred forms as identified above.

In the forms of the invention described above, the particulate product may have, in one form, both actives in a crystalline form. Applicants have discovered that the method of the present invention can be used to produce a product containing particles of two or more pharmaceutically active compounds, and where at least 95% of the fine particle fractions (Stages 3 to 8 on the cascade impactor), has a controlled drug ratio, with both actives in a crystalline form. In particular, a product having formoterol fumarate and budesonide in a 1:18 mass ratio is formed, the particles of the product having substantially uniform appearance under SEM (Scanning Electron Microscopy) and 95% of the particles having a size of 1.2-6.5 µm (Stages 3 to 6 on the cascade impactor) at the predetermined drug ratio.

The method of the present invention may further include coformulating two pharmaceutically active compounds together with an excipient (which may itself be a pharmaceutically active compound) or a coating material, or the coformulation of more than two pharmaceutically active compounds. The method of the present invention may also further include using the dense fluid to coformulate two or more pharmaceutically active components together with an excipient or a coating material.

The excipient may be of any suitable type, including, but not limited to ionic and non-ionic surfactants, polymers, natural products and oligomers. In one embodiment, the excipient is an ionic or non-ionic surfactant. Typical surfactants include, but are not limited to, the oleates, stearates, myristates, alkylethers, alklyarylethers and sorbates and any combination of the above. In a preferred embodiment, the surfactant is a polyoxyethylene sorbitan fatty acid ester, such as Tween 20 or Tween 80, sorbitan monooleate (SPAN-80) or isopropyl myristate. In another preferred embodiment, suitable excipients include polyvinylpyrrolidone (PVP, Povidone), polyethylene glycol (PEG) (for example polyethylene glycol 600), microcrystalline cellulose, cellulose, cellulose acetate, cyclodextrin, hydroxypropyl beta cyclodextrin, lecithin, magnesium stearate, lactose, mannitol, trehalose and the like and any combination of the above.

The method of the present invention preferably produces a product in a form suitable for inhalation delivery, for example, for delivery by a dry powder inhaler, a metered dose inhaler, or a nebuliser. In one embodiment, the invention provides a product having two or more pharmaceutically active compounds in the ratios given above, wherein at least 80%, preferably 90%, more preferably 95% of the inhalable mass fraction of the product are between 1.2 and 6.5 μm in size (Stages 3 to 6 of the cascade impactor).

In addition, the invention extends to a product produced by the methods described above.

In another aspect of the present invention, there is provided an apparatus which may be used with the method of the present invention. In one embodiment there is provided an apparatus for forming a product containing two or more components including a precipitation chamber, the precipitation chamber being connected to three or more conduits, wherein the three or more conduits are arranged such that the conduits enter the precipitation chamber in close proximity to each other. In a preferred embodiment of this aspect of the present invention, the three or more conduits enter the precipitation chamber at substantially the same point.

In another embodiment there is provided an apparatus for forming a particulate product containing two or more components including a precipitation chamber, the precipitation chamber being connected to three or more conduits, each conduit having an exit in to the precipitation chamber and being adapted to carry a stream of a dense fluid, solution or suspension, and wherein the three or more conduits are arranged such that after each stream exits its conduit, the three or more streams intersect at substantially the same point.

In a further aspect, the apparatus has means to convey the fine particles from the precipitation chamber to at least one particle collection chamber, downstream of the precipitation chamber, the particle collection chamber having an inlet and an outlet separate from the inlet. In one embodiment, the outlet is disposed above the inlet in use of the apparatus, such that gravity exerts a force generally towards the inlet on particles adjacent the outlet. In a further form of the invention, the apparatus further includes at least two particle collection chambers in parallel with each other and each able to be connected in series with the precipitation chamber.

Preferably, the or each particle collection chamber has an inlet and an outlet separate from the inlet, in which the fine particles and dense fluid pass through the inlet and the flow of dense fluid through the outlet is adjusted to maximise the proportion of fine particles collectable from the second collection chamber.

Within the collector device or collection chamber, the particles are largely suspended by the force exerted on them by a flow of dense gas in one direction, which force is generally balanced by a second force. This second force may be gravity (ie, the particles' weight) where the collection chamber is orientated such that the outlet is above the inlet when the collection chamber is connected to (or on-line with) the particle formation apparatus. Such a force could also be generated by other means, eg. centrifugal force with an appropriate arrangement of the collection chamber(s), and such an arrangement would allow variation of this second balancing force. Where the particles are charged, electromagnetic forces may be employed. As will be appreciated by one skilled in the art, the objective is to balance the force on particles of the carrying fluid, which otherwise tends the particles either to "cake" at one end of the collection chamber and/or to escape through the outlet with the carrying fluid. Therefore, the newly formed particles do not "fall" on top of the previously formed particles and are not subjected to a pressure which could deform their shape and are also less susceptible to aggregation.

In another embodiment, the method is conducted wherein the fine particles flow with the dense gas from a first chamber in which the particles are formed to a second collection chamber, from which the particles are collected. Preferably, the second collection chamber has an inlet and an outlet separate from the inlet, in which the fine particles and dense fluid pass through the inlet and the flow of dense fluid through the outlet is adjusted to maximise the proportion of fine particles collectable from the second collection chamber. In a preferred embodiment, one of the conduits carries a stream of dense fluid, a second conduit carries a stream of a solution and a third conduit carries a stream of a suspension.

Preferably the product is formed by contacting a dense fluid with a suspension of a first active compound in a solvent and a solution of a second active compound in a solvent.

In a preferred embodiment, the first or second actives, preferably both, are retained in a crystalline form. Particles produced by the method of the invention may retain both the first and second active in a crystalline form. In other embodiments, amorphous forms of the first and/or second active may be produced. For example, the active that is in solution may be transformed into an amorphous form when precipitated in the precipitation chamber.

In another embodiment, there is further provided a mixing device (for example, an impellor, mixer or stirrer) in the precipitation chamber so as to improve mass transfer rates in the chamber.

In another preferred embodiment, there is provided particle collection chambers that are inverted such that a fluidised bed is created from the particles in motion with the antisolvent. These chamber(s) have an inlet connected to the precipitation chamber and a filter at their outlet to trap particles.

It will be understood that the invention disclosed and defined in this specification extends to all alternative combinations of two or more of the individual features mentioned or evident from the text or drawings. All of these different combinations constitute various alternative aspects of the invention. Various other modifications and/or alterations may be made without departing from the spirit of the present invention as outlined herein.

BRIEF DESCRIPTION OF THE DRAWINGS

FIG. 5 is a graph showing the deposition profile of the neat formoterol fumarate/budesonide combination product (Example 2) in the dry powder aerosol performance test apparatus.

FIG. 6 is a graph showing the formoterol fumarate to budesonide mass ratio in the various stages of the dry powder aerosol performance test apparatus with the combination product (Example 2).

Examples of the invention will now be described for greater clarity of the description of the invention. The examples do not limit the scope of the invention described.

EXAMPLE 1

Figure 1:
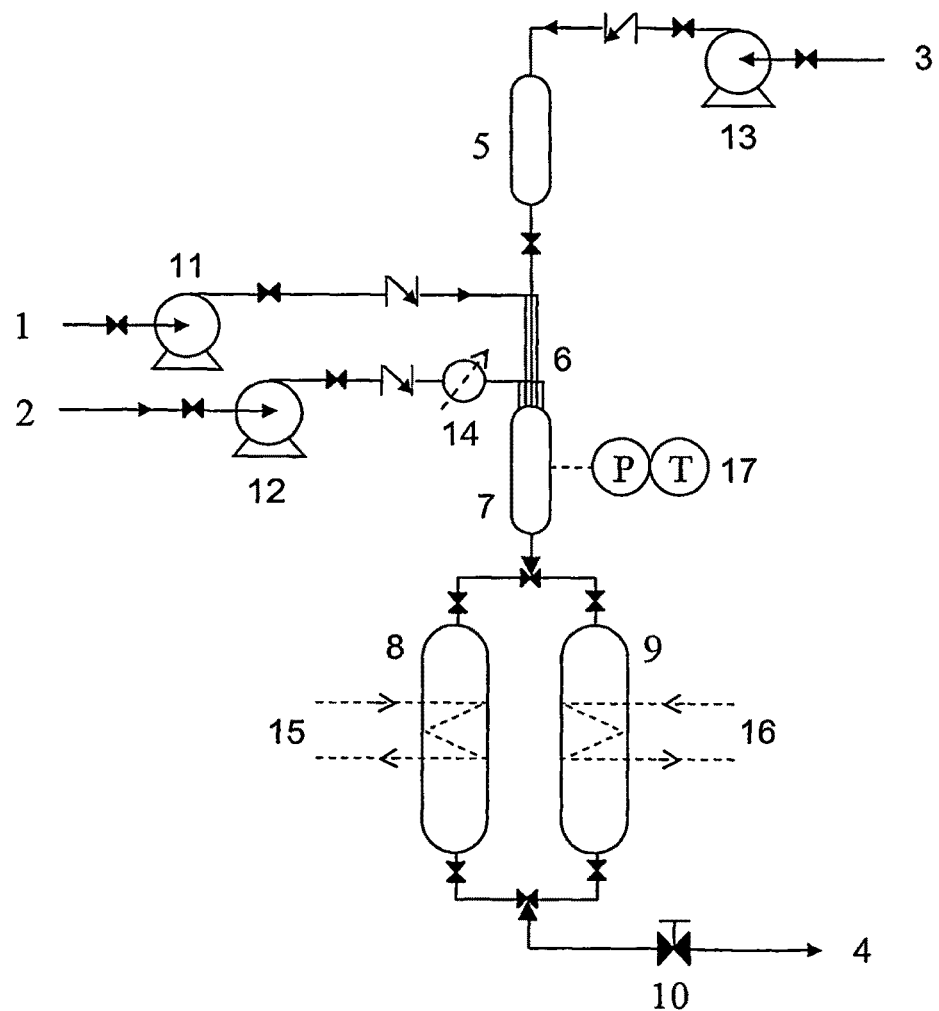
FIG. 1 is a schematic diagram of the suspension spraying apparatus.

The apparatus used in the method of the present invention is shown schematically in FIG. 1. The apparatus includes a precipitation chamber 7 which is connected via delivery device 6 to three conduits.

The first conduit 2 provides a flow of dense fluid to the delivery device 6 which, in turn, delivers the dense fluid into the precipitation chamber 7. The pressure of the dense fluid in conduit 2 is controlled by a high pressure pump 12. Before entering the precipitation chamber 7, the dense fluid in conduit 2 is adjusted to the operating temperature by a heat exchanger 14.

The second conduit 1 provides a flow of a solution of the second active compound to the delivery device 6 which, in turn, delivers the solution into the precipitation chamber 7. The flowrate and pressure of the solution in conduit 1 is controlled by a high pressure pump 11.

The third conduit 3 connects to a suspension chamber 5, which contains the first active compound in a suspension medium. A flow of pressurised dense fluid through conduit 3 then drives the first active compound in its suspension medium into the delivery device 6 which, in turn, delivers the first active compound in its suspension medium into precipitation chamber 7.

Figure 2:
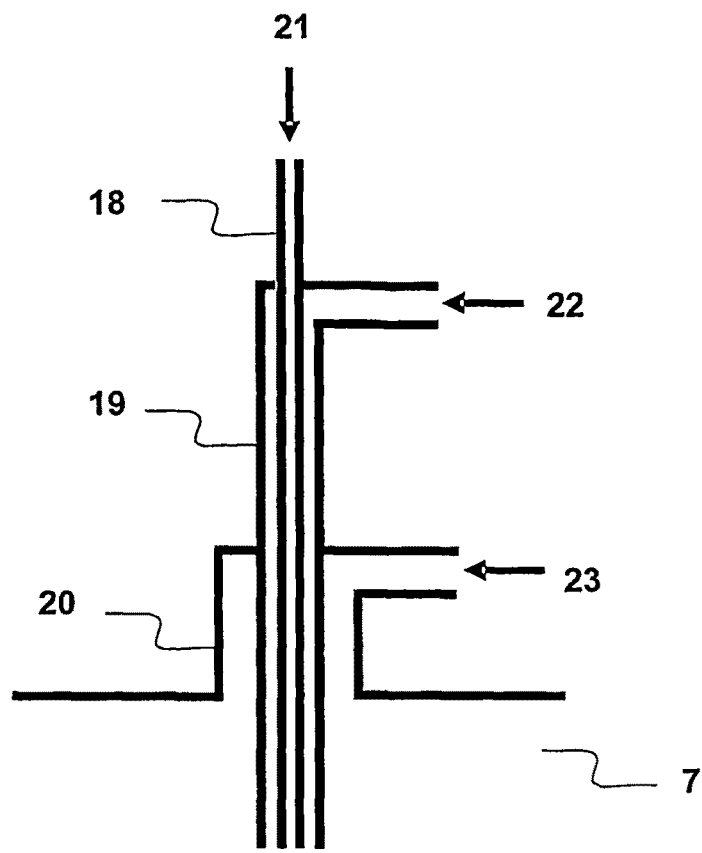
FIG. 2 is a schematic diagram of the three-fluid delivery device used as part of the suspension spraying apparatus.

The delivery device 6 may be any system which delivers all three conduits into precipitation chamber 7 within close proximity to each other. In this example, the delivery device 6 is a so-called "three-fluid" delivery device, shown schematically in FIG. 2. The delivery device 6 consists of a standard 1/16" stainless steel tube within a wide bore 1/8" stainless steel tube. The 1/8" tube is connected to a standard 1/4" Swagelok® fitting (Ohio, USA) which is connected to precipitation chamber 7. In use in the method of the present invention, the suspension of the first active compound 21 enters the precipitation chamber 7 via the inner 1/16" tube 18. The solution of the second active compound 22 enters the precipitation chamber 7 via the 1/8" tube 19, and the dense fluid 23 enters the precipitation chamber 7 via the 1/4" fitting 20. The three fluid streams are thus kept separate from one another while in the delivery device 6. The tips of the 1/16" and the 1/8" tubing (18, 19) are flush, such that the suspension and solution emerge together and mix with the dense fluid. The tips of tubes 18 and 19 protrude into the precipitation chamber 7. Upon mixing, the particulate product, consisting of the first active compound and the second active compound is precipitated. The pressure and temperature of the precipitation chamber 7 is monitored by sensor 17 which is located downstream of the delivery device and is connected to the precipitation chamber 7.

Two product separation vessels 8, and 9, are connected, in parallel, to and downstream of the precipitation chamber 7. Each separation vessel allows the product that has been precipitated in the precipitation chamber 7 to be retained in the separation vessel while the rest of the contents are passed through it further downstream. In this example each product separation vessel contains a stainless steel filtration element that is located within each of the separation vessels 8 and 9. The nominal pore size of the filtration elements is 0.5 micron. The product separation vessels, 8 and 9, may be used to separate and accumulate product either one at a time (ie, sequentially, thereby running the process continuously), or simultaneously (ie, batchwise) by opening and/or closing the isolation valves located on either end of the vessels. Both product separation vessels, 8 and 9, may be cooled or heated to maintain operating temperature by heat exchangers 15 and/or 16. The metering valve 10 controls the flowrate of conduit 4 which exits the product separation vessels 8 and 9. Conduit 4 then enters a waste line (not shown).

In operation of the apparatus, the heat exchangers 14, 15 and/or 16 are set to the desired operating temperature. The dense fluid is then allowed to flow through conduit 2 into precipitation chamber 7. The dense fluid in the precipitation chamber 7 is pressurised using the high pressure pump 12. Metering valve 10 is adjusted to provide the operating flow rate of the dense fluid.

The solution of the second active compound in conduit 1 is pressurised by high pressure pump 11. At the same time, the suspension of the first active compound in suspension chamber 5 is pressurised by high pressure pump 13. Once the solution and suspension are at operating pressure, both are allowed into the precipitation chamber 7, via delivery device 6, at constant flow rates. When sufficient particulate product has been precipitated and collected in the product separation vessels 8 and/or 9, the flow of the solution through conduit 1 and the suspension from the suspension chamber 5 is ceased. The flow of dense fluid through conduit 2 is continued until a sufficient volume of dense fluid has passed through the system to remove all traces of solvent from the product and the product separation vessels 8 and/or 9. The apparatus is then depressurised via metering valve 10 until ambient pressure is reached. The product may then be harvested by any appropriate means. For example, the apparatus may then be disassembled to remove the product from the product precipitation vessels 8 and/or 9.

EXAMPLE 2

Figure 5:
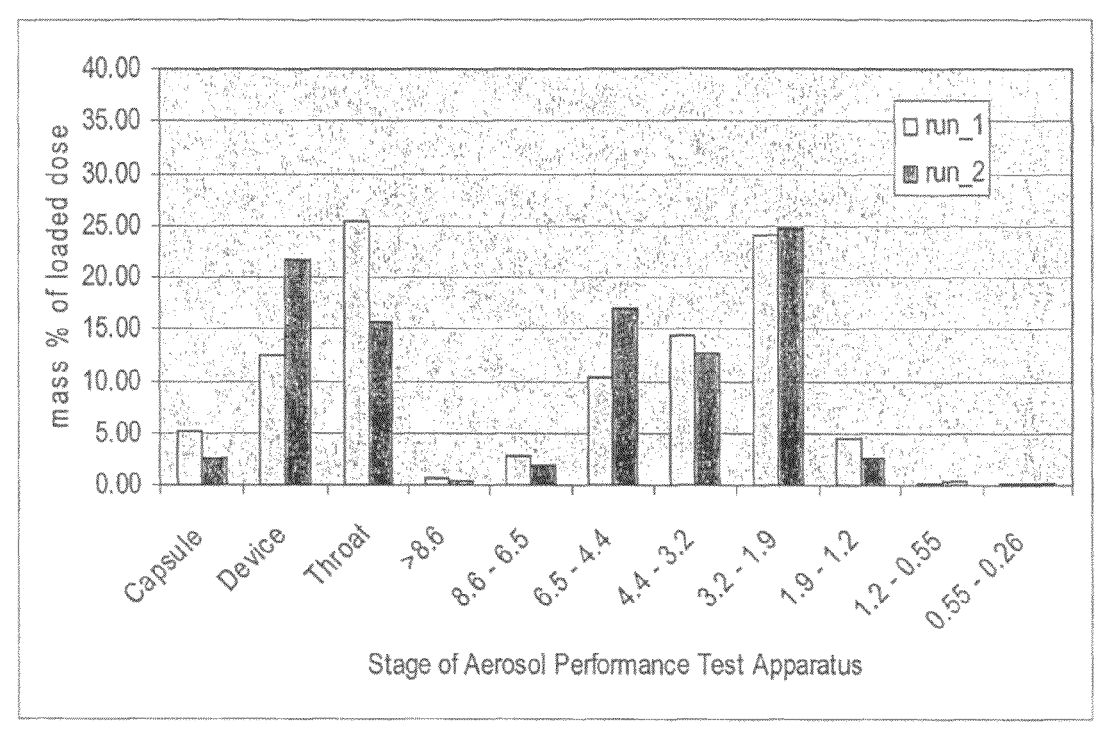
Figure 6:
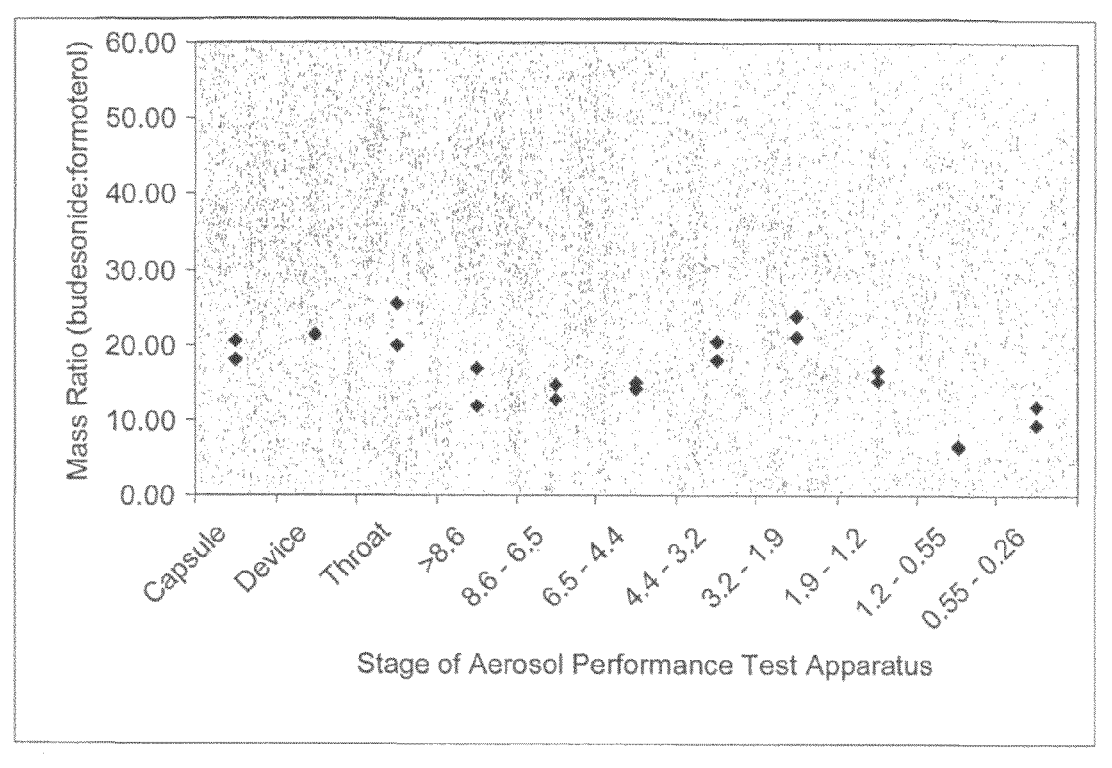

Dichloromethane was used as the suspension medium and solvent for formoterol fumarate and budesonide respectively. A 1.5 mg/mL formoterol/dichloromethane suspension was made by sonicating the formoterol in the dichloromethane for 1 minute and this suspension was used as the suspension of the first active, which was delivered into the precipitation vessel. A 30 mg/mL budesonide/dichloromethane solution was made and used as the solution of the second active, which was delivered into the precipitation vessel at. The flow rates at which both the suspension and solution were delivered into the precipitation vessel were equal. Carbon dioxide was used as the dense fluid, which was delivered into the precipitation vessel and product separation vessels. The ratio between the flowrate of each of the two suspension and solution streams and the flowrate of the carbon dioxide was between about 1:100 to 1:130. The operating pressure and temperature was 85 bar and 40° C. The suspension of the first active and the solution of the second active were precipitated for 2.5 hours, followed by 20 to 25 minutes of solvent removal with fresh carbon dioxide at operating pressure and temperature. The carbon dioxide flow was then ceased and the system was depressurised. The precipitation and product separation vessels were disassembled and the particulate product was collected. The resultant product has a formoterol to budesonide mass ratio of about 1:20. The physical and thermal characteristics of the formoterol/budesonide product are shown in FIGS. 3-6 and in Table 2. The product was in the form of a fine, white, easily-dispersible powder consisting of mainly toroidal-shaped particles of less than 5 micron when viewed under SEM. The product had a major single endothermic peak at approximately 256.0° C. and two phase transition points at approximately 82.5 and 127.8° C. which resembled the thermal changes observed for crystalline formoterol. In an Aerolizer device tested with an Anderson Cascade Impactor with pre-separator and eight stages (refer to Table 1 for the parameters used), the product, in its dry powder, neat form had an average emitted dose of 79.2% by mass, an average fine particle fraction of 70.6% by mass (as a percentage of the emitted dose), and an average fine particle fraction of 55.8% by mass (as a percentage of the loaded dose). These performance figures are shown in Table 2. Corresponding device deposition profiles of the combination product are shown in FIG. 5. The budesonide to formoterol mass ratio in each of the stages of the aerosol performance test device is shown in FIG. 6. It is noteworthy that at least 95% by mass of the fine particle fraction deposited on stages 3-6 inclusively (corresponding to the approximate particle size range 1.2-6.5 micron), and that on each of these stages the formoterol to budesonide mass ratio was consistent (within reasonable bounds), at about 1:19. The actual mass ratio of the total combined fine particle fractions (from Stages 3 to 8 inclusive) was determined by HPLC analysis to be within 5% of the target ratio of 1:20.

TABLE 1

A list of the method parameters used in the dry powder aerosol performance tests.

| | |
|---|---|
| Dry powder device | Aerolizer (Novartis, fitted snout) |
| Loaded dose, mg | 10 ± 1 |
| Capsule type | Gelatin, size no. 3 |
| Cascade impaction device | Anderson cascade impactor with pre-separator and 8 stages |
| Air flowrate, L/min | 60 |
| Coating on plates | Propylene glycol |
| Filter type | Glass fibre |
| Actuation period, s | 60 |
| No. of actuations per run | 1 |
| No. of replicates | 2 |
| Wash solvent | Methanol (technical grade) |

TABLE 2

A list of the aerosol performance indices and data of the neat formoterol/budesonide combination product in the dry powder aerosol performance test apparatus.

| Performance Index | Run 1 | Run 2 | Average |
|---|---|---|---|
| % ED | 82.5 | 75.9 | 79.2 |
| % FPF of ED | 65.2 | 76.0 | 70.6 |
| % FPF of LD | 53.8 | 57.7 | 55.8 |

TABLE 3

A list of the definitions and analytical derivations used as the performance indicators for the dry powder aerosol performance tests.

| | |
|---|---|
| Loaded dose, LD | Total mass recovered |
| Emitted dose, ED | Total mass recovered in the Throat and 8 collection plates of the cascade impactor apparatus |
| Fine particle fraction, FPF | Total mass recovered from the collection plates 3 to 8 |
| % ED | ED/LD × 100 |
| % FPF of ED | FPF/ED × 100 |
| % FPF of LD | FPF/LD × 100 |

EXAMPLE 3

A suspension of formoterol fumarate and a solution of fluticasone propionate was used as the suspension of the first active and the solution of the second active respectively. All other parameters were the same as in Example 2 above. The product appeared as particles of a suitable particle size distribution for inhalation (generally less than 5 micron diameter) and was characterised by a clear endothermic event occurring at approximately 266° C. on a DSC thermogram.

EXAMPLE 4

A suspension of salmeterol xinafoate and a solution of fluticasone propionate was used as the suspension of the first active and the solution of the second active respectively. All other parameters were the same as in Example 2 above. The product appeared as particles of a suitable particle size distribution for inhalation (generally less than 5 micron diameter) and was characterised by a clear endothermic event occurring at approximately 266° C. on a DSC thermogram.

EXAMPLE 5

A suspension of salmeterol xinafoate and a solution of budesonide was used as the suspension of the first active and the solution of the second active respectively. All other parameters were the same as in Example 2 above. The product appeared as particles of a suitable particle size distribution for inhalation (generally less than 5 micron diameter) and was characterised by a clear endothermic event occurring at approximately 256° C. on a DSC thermogram.

EXAMPLE 6

Figure 3:
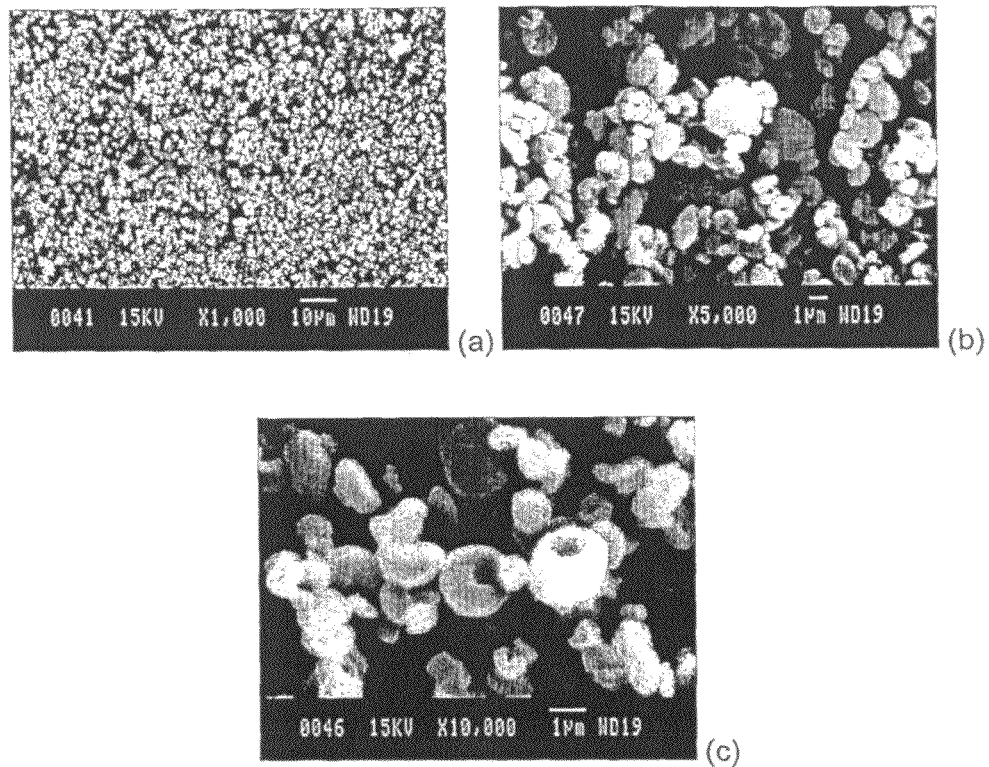
FIG. 3 is a collection of 3 scanning electron microscope images of the formoterol budesonide combination product (Example 2) at high magnifications, namely (a) 1,000 times, (b) 5,000 times and (c) 10,000 times.
Figure 4:
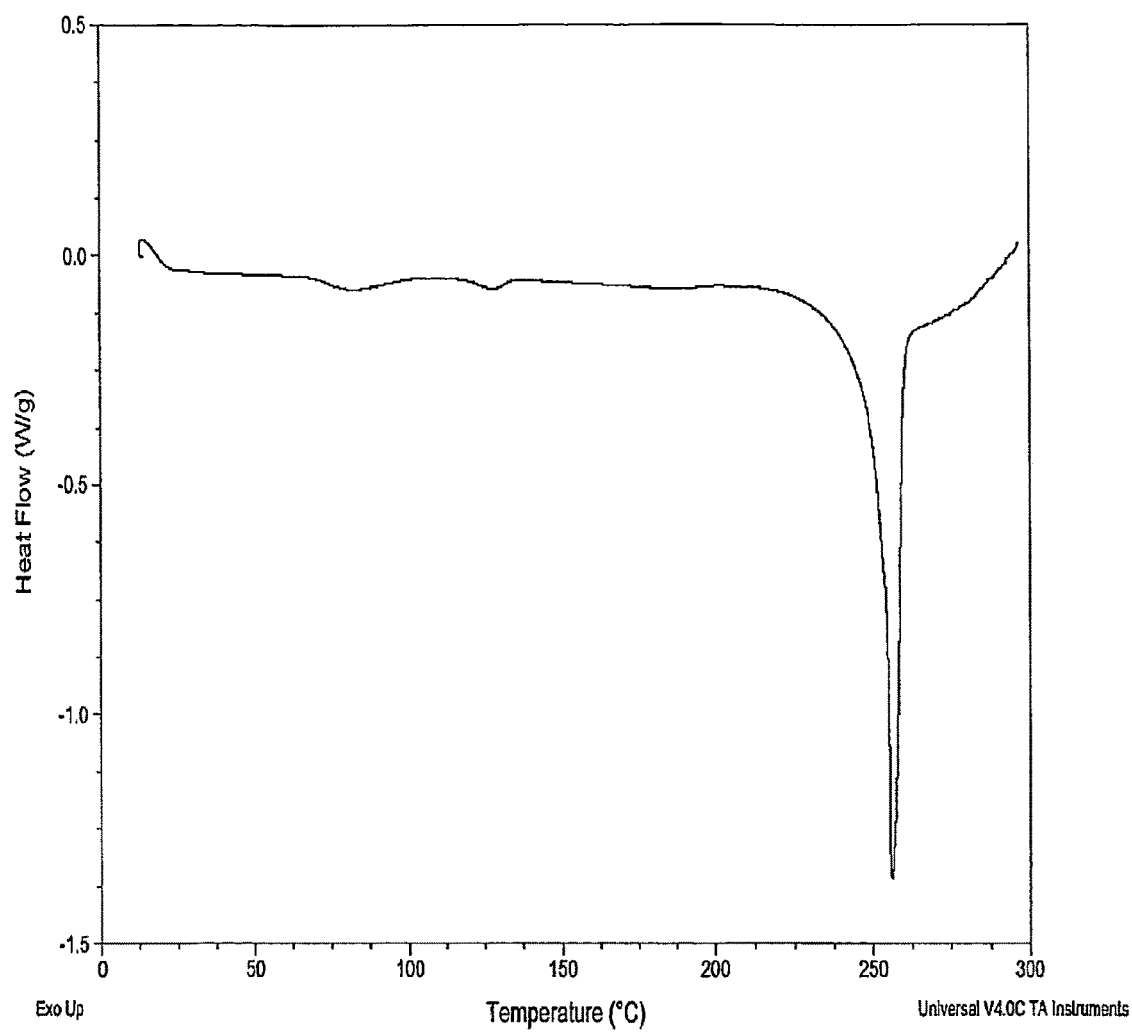
FIG. 4 is a thermogram of the product (Example 2) showing the characteristic phase transition temperatures of crystalline formoterol and budesonide.

The production parameters such as flowrate of dense gas through the precipitation chamber and the cross-sectional diameter of the precipitation chamber are such that the flow in the precipitation chamber is laminar. Laminar flow in the precipitation chamber can ensure that particle formation in the chamber creates particles of a predominantly toroidal morphology which are favourable for inhalation as shown in FIG. 3. Hence for a precipitation chamber of any cross-sectional diameter, D, the flowrate of dense gas through it can be any flowrate as long as the flow through the chamber is laminar.

The flow characteristic in the precipitation chamber can be measured by the Reynolds number, Re, a dimensionless number commonly used in fluid mechanics that indicates whether a fluid flow in a particular situation is laminar or turbulent. Flow with a Reynolds number less than 2000-4000 is laminar. Flow with a Reynolds number greater than 2000-4000 is turbulent. Flow with a Reynolds number between 2000-4000 is in a transition state. The Reynolds number may also be used to indicate the ratio of the shear stress due to turbulence to the shear stress due to viscosity of the fluid, or as a ratio of inertial forces to viscous forces in a flowing fluid, and as such, is calculated using the following equation:

$$Re = 4\rho F / \pi D \mu$$

Where $\rho$ is the density of the fluid, F, the free-stream volumetric flowrate of the fluid, $\pi$, the Pi constant, D, the cross-sectional diameter of the vessel, and $\mu$, the dynamic viscosity of the fluid.

Hence when a higher flowrate (F) is used a larger diameter (D) precipitation chamber would be required to maintain the same flow conditions (Reynolds number, Re) in the larger chamber in order to produce the same product, and vice versa. To obtain a product with toroidal morphology as that shown in FIG. 3, laminar flow must be maintained in the precipitation vessel. Two examples of laminar flow in the precipitation chamber are as follows: $\rho=500$ kg/m$^3$, F=6.61×10$^{-7}$ m$^3$/s, D=0.015 m, $\mu=2\times10^{-5}$ kg/ms (the Re is approximately 1400), and when $\rho=500$ kg/m$^3$, F=5.29×10$^4$ m$^3$/s, D=0.0916 m, p=2×10$^{-5}$ kg/ms (the Re is 1840).

All other parameters were the same as in Example 2 above. Deviations from a laminar flow regime in the precipitation chamber, such as transitional or turbulent flow, lead to deviations from toroidal morphology in the product produced.

EXAMPLE 7

Dichloromethane was used as the suspension medium and solvent for formoterol fumarate and budesonide respectively. A 1.67 mg/mL formoterol/dichloromethane suspension was made by sonicating the formoterol in the dichloromethane for 1 minute and this suspension was used as the suspension of the first active, which was delivered into the precipitation vessel. All other parameters were the same as in Example 2 above.

Figure 7:
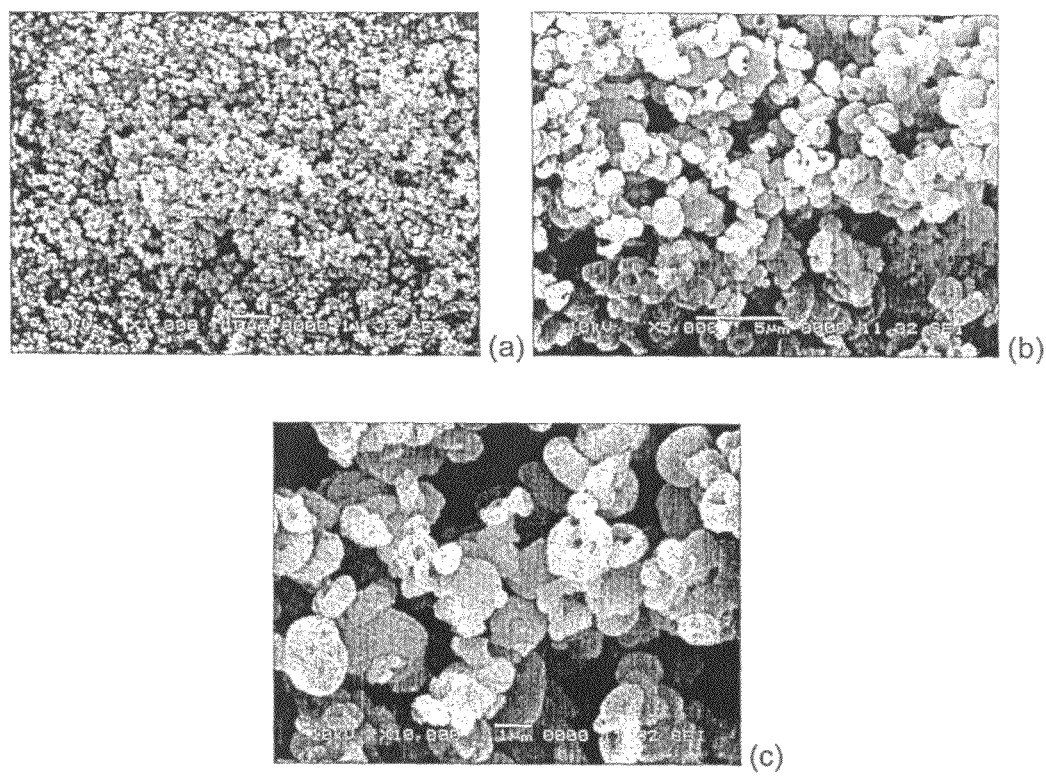
FIG. 7 is a collection of 3 scanning electron microscope images of the product of Example 7, namely (a) 1,000 times, (b) 5,000 times and (c) 10,000 times.
Figure 8:
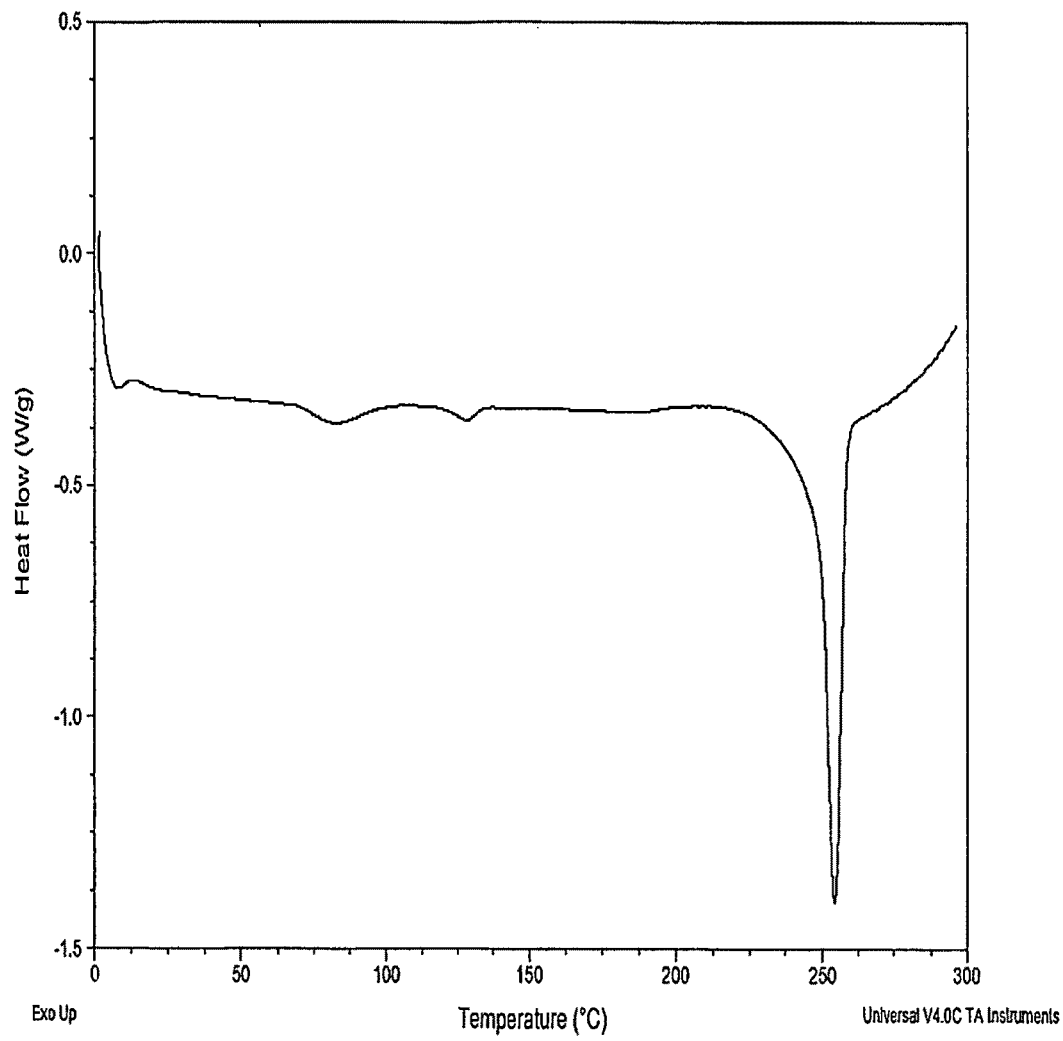
FIG. 8 is a thermogram of the product (Example 7) shown in FIG. 7 showing its characteristic phase transition temperatures.
Figure 9:
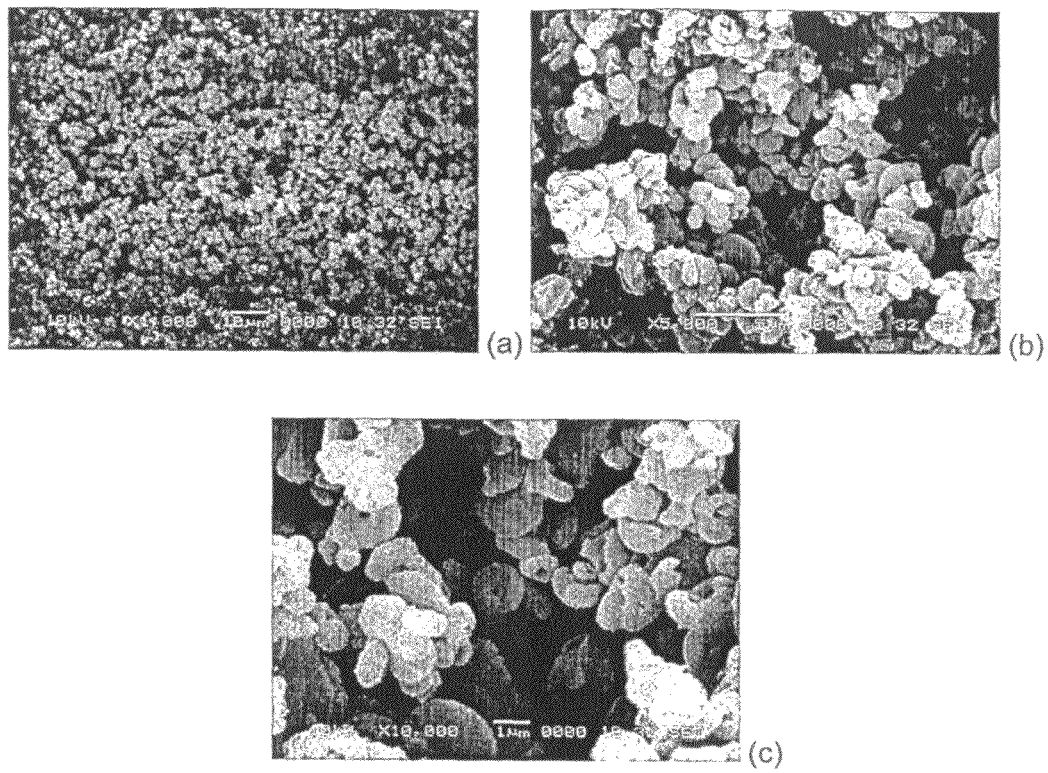
FIG. 9 is a collection of 3 scanning electron microscope images of the product of Example 8, namely (a) 1,000 times, (b) 5,000 times and (c) 10,000 times.
Figure 10:
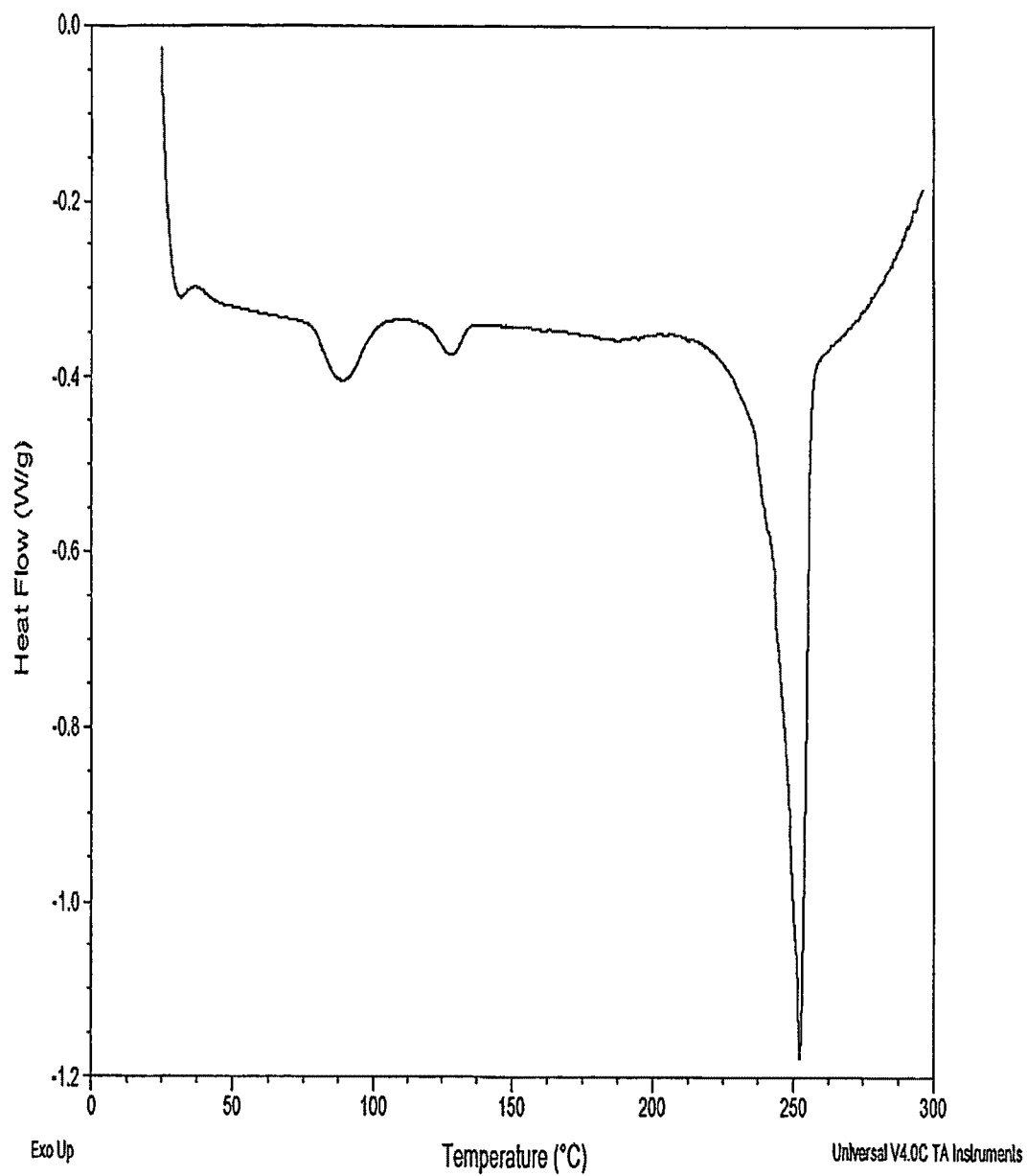
FIG. 10 is a thermogram of the product (Example 8) shown in FIG. 9 showing its characteristic phase transition temperatures.

The resultant product has a measured formoterol to budesonide mass ratio of 1:18 (mass formoterol to budesonide). The physical and thermal characteristics of the formoterol/budesonide product are shown in FIGS. 7 and 8. The product was in the form of a fine, white, easily-dispersible powder consisting of mainly toroidal-shaped particles of less than 5 micron when viewed under SEM. The product had a major single endothermic peak at approximately 253.9° C. and two phase transition points at approximately 82.7 and 127.7° C. which resembled the thermal changes observed for crystalline formoterol.

EXAMPLE 8

Dichloromethane was used as the suspension medium for formoterol fumarate and a surfactant (Tween 80) dichloromethane solution as the solvent for budesonide. A 2 mg/mL formoterol/dichloromethane suspension was made by sonicating the formoterol in the dichloromethane for 1 minute and this suspension was used as the suspension of the first active, which was delivered into the precipitation vessel. A 30 mg/mL budesonide/dichloromethane/surfactant (Tween 80) solution was made where the concentration of surfactant to budesonide was less than 0.04% (by mass of surfactant to mass of budesonide in solution) and used as the solution of the second active, which was delivered into the precipitation vessel. All other parameters were the same as in Example 2 above.

The resultant product has a measured formoterol to budesonide mass ratio of around 1:15. The physical and thermal characteristics of the formoterol/budesonide product are shown in FIGS. 9 and 10. The product was in the form of a fine, white, easily-dispersible powder consisting of mainly toroidal-shaped particles of less than 5 micron when viewed under SEM. The product had a major single endothermic peak at approximately 252.1° C. and two phase transition points at approximately 89.8 and 127.8° C. which resembled the thermal changes observed for crystalline formoterol.

The yield improved to at least 80% with the presence of Tween 80 surfactant in the spraying solution and consistent toroidal morphology of the particles is maintained for extended periods of production.

The invention claimed is:

1. A method of coformulating two or more pharmaceutically active compounds to form a particulate product, the method comprising:

i) contacting a dense fluid with:

a) a suspension of a first active compound in a suspension medium that is miscible with the dense fluid; and b) a solution of a second active compound in a solvent that is miscible with the dense fluid; such that precipitation of the second active in the presence of the first active occurs, wherein the contacting is under laminar flow conditions, thereby forming a particulate product.

2. The method of claim 1, wherein the dense fluid is an anti-solvent.

3. The method of claim 1, wherein the solution further includes a surfactant.

4. The method of claim 1, wherein the particulate product comprises a physical interaction between the first active compound and the second active compound.

5. The method of claim 4, wherein the second active compound partially or fully coats the first active compound in the particulate product.

6. The method of claim 1, wherein the ratio of the first active compound: second active compound in the particulate product is between 1:1 and 1:100 w/w.

7. The method of claim 1, wherein the first active compound and the second active compound are in a crystalline form in the particulate product.

8. The method of claim 1, wherein the first active compound and the second active compound are a $\beta$-agonist and a corticosteroid respectively.

9. The method of claim 1, wherein the suspension medium and solution are miscible with each other.

10. The method of claim 1, wherein the method is conducted with a flowrate ratio of the suspension of the first active compound or the solution of the second active compound to the dense fluid of between about 1:10 to about 1:5000.

11. The method of claim 1, wherein the method is conducted with a flowrate ratio of the suspension of the first active compound or the solution of the second active compound to the dense fluid of between about 1:50 to about 1:1000.

12. The method of claim 1, wherein the method is conducted with a flowrate ratio of the suspension of the first active compound or the solution of the second active compound to the dense fluid of between about 1:80 to about 1:200.

13. The method of claim 12, wherein the method is conducted at a temperature of between about 0° C. and about 100° C. and a pressure of between about 1 bar to about 500 bar.

14. The method of claim 1, wherein the particulate product formed by contacting the solution, suspension and dense fluid, flows from a first chamber in which the particles are formed to a second collection chamber, wherein the particles are suspended in the second chamber by a force exerted on them by a flow of dense fluid in one direction, which force is balanced by a second force exerted on the particle.

15. A particulate product produced by the method of claim 1.

16. The particulate product of claim 1, wherein the first active compound is a $\beta$-agonist and the second active compound is an anti-inflammatory agent.

17. The particulate product of claim 1, wherein the first active is formoterol fumarate and the second active is budesonide.

18. A pharmaceutical composition comprising the particulate product of claim 1.

19. An apparatus for forming a particulate product containing two or more components including a precipitation chamber, the precipitation chamber being connected to three or more conduits, each conduit having an exit in to the precipitation chamber and being adapted to carry a stream of a dense fluid, solution or suspension, and wherein the three or more conduits are arranged such that after each stream exits its conduit, the three or more streams intersect at substantially the same point, the apparatus also having means to convey the fine particles from the precipitation chamber to at least one particle collection chamber, downstream of the precipitation chamber, the particle collection chamber having an inlet and an outlet separate from the inlet in which the outlet is disposed above the inlet in use of the apparatus, such that gravity exerts a force generally towards the inlet on particles adjacent the outlet.

20. The apparatus of claim 19, further at least two particle collection chambers.

21. The apparatus of claim 20, wherein the particle collection chambers are connected in parallel with each other and each particle collection chamber is connected in series with the precipitation chamber.

22. The apparatus of claim 19, wherein the at least one particle collection chamber is inverted such that the particles create a fluidized bed.

23. The apparatus of claim 19, wherein each of the conduits carrying the solution and the suspension each comprise a terminal tip, the tips being flush with one another and extend into the precipitation chamber.

24. The apparatus of claim 23, wherein the conduit carrying the dense fluid comprises a terminal tip, the tip being flush with an inner surface of the precipitation chamber.

25. The apparatus of claim 19, wherein the conduit carrying the solution and the suspension are housed within the conduit carrying the dense fluid and protrude further into the precipitation chamber than the conduit carrying the dense fluid.

26. A method of coformulating two or more pharmaceutically active compounds into a particulate product, the method comprising contacting a dense fluid with:
 a suspension of a first active compound in a suspension medium that is miscible with the dense fluid, wherein the first active compound is formoterol fumarate and the suspension medium is dichloromethane; and
 a solution of a second active compound in a solvent that is miscible with the dense fluid, wherein the second active compound is budesonide and the solvent is dichloromethane; such that precipitation of the second active in the presence of the first active is induced, and wherein the dense fluid is carbon dioxide, and wherein further the contacting is conducted under laminar flow conditions with a flowrate ratio of the suspension or the solution to the dense fluid between about 1:100 to about 1:130.

* * * * *

UNITED STATES PATENT AND TRADEMARK OFFICE
CERTIFICATE OF CORRECTION

PATENT NO. : 8,475,845 B2  
APPLICATION NO. : 11/995676  
DATED : July 2, 2013  
INVENTOR(S) : Tu et al.

Page 1 of 1

It is certified that error appears in the above-identified patent and that said Letters Patent is hereby corrected as shown below:

TITLE PAGE

Item (86) Delete "PCT/US2006/000998" and replace with --PCT/AU2006/000998--.

Signed and Sealed this  
Third Day of September, 2013

Teresa Stanek Rea  
*Acting Director of the United States Patent and Trademark Office*

UNITED STATES PATENT AND TRADEMARK OFFICE
CERTIFICATE OF CORRECTION

PATENT NO.          : 8,475,845 B2                                              Page 1 of 1
APPLICATION NO.     : 11/995676
DATED               : July 2, 2013
INVENTOR(S)         : Tu et al.

It is certified that error appears in the above-identified patent and that said Letters Patent is hereby corrected as shown below:

ON THE TITLE PAGE

Item (86) in Column 1, Line 1, under PCT No.:, delete "PCT/US2006/000998" and replace with --PCT/AU2006/000998--.

Item (60) In Column 1, Line 1, under Related U.S. Application Data, delete "60/669,734," and replace with --60/699,734,--.

Item (57) in Column 2, Line 3, under ABSTRACT, delete "With" and replace with --with--.

IN THE SPECIFICATION

In Column 2, Line 35, delete "time;" and replace with --time,--.

In Column 4, Lines 38-39, delete "aminopropryonic" and replace with --aminopropionic--.

In Column 8, Line 51, delete "alklyarylethers" and replace with --alkylarylethers--.

In Column 9, Line 37, delete "the or".

In Column 15, Line 4, delete "p" and replace with --μ--.

Signed and Sealed this
Eleventh Day of March, 2014

Michelle K. Lee
*Deputy Director of the United States Patent and Trademark Office*